(12) United States Patent
Nylese

(10) Patent No.: US 7,700,372 B2
(45) Date of Patent: Apr. 20, 2010

(54) PORTABLE DIAGNOSTIC DEVICE AND METHOD FOR DETERMINING TEMPORAL VARIATIONS IN CONCENTRATIONS

(76) Inventor: Tara Nylese, 819 Chestnut Ct., Marco Island, FL (US) 34145

( * ) Notice: Subject to any disclaimer, the term of this patent is extended or adjusted under 35 U.S.C. 154(b) by 294 days.

(21) Appl. No.: 10/530,464

(22) PCT Filed: Oct. 8, 2003

(86) PCT No.: PCT/US03/31859

§ 371 (c)(1),
(2), (4) Date: Apr. 5, 2005

(87) PCT Pub. No.: WO2004/034056

PCT Pub. Date: Apr. 22, 2004

(65) Prior Publication Data

US 2006/0024842 A1 Feb. 2, 2006

Related U.S. Application Data

(60) Provisional application No. 60/416,676, filed on Oct. 8, 2002.

(51) Int. Cl.
*C12Q 1/68* (2006.01)
*G01N 21/00* (2006.01)
*B01L 3/00* (2006.01)
*B01L 9/00* (2006.01)
*G01N 15/06* (2006.01)
*C12Q 1/00* (2006.01)
*G01N 33/53* (2006.01)
*C12M 1/34* (2006.01)
*C12M 3/00* (2006.01)
*G01N 33/566* (2006.01)
*G01N 33/543* (2006.01)

(52) U.S. Cl. ........................... 436/518; 422/50; 422/55; 422/58; 422/61; 422/68.1; 422/104; 435/4; 435/7.1; 435/287.1; 435/287.2; 435/287.7; 435/288.2; 435/288.7; 436/501; 436/164; 436/807

(58) Field of Classification Search .................. 422/50, 422/55, 58, 61, 68.1, 104; 435/4, 7.1, 287.1, 435/287.2, 287.7, 288.2, 288.7; 436/501, 436/164, 807, 518
See application file for complete search history.

(56) References Cited

U.S. PATENT DOCUMENTS 3,006,735 A * 10/1961 Jordan ........................ 436/79
(Continued)

FOREIGN PATENT DOCUMENTS

| WO | WO/93/15230 | 8/1993 |
| WO | WO 98/39657 | 9/1998 |

OTHER PUBLICATIONS

Dart et al. "Rate of Change of Serial b-Human Chorionic Gonadotropin Values as a Predictor of Ectopic Pregnancy in Patients with Indeterminate Transvaginal Ultrasound Findings," Annals of Emergency Medicine, vol. 34, No. 6 (1999) 703-710.*

*Primary Examiner*—Mark L Shibuya
*Assistant Examiner*—Jacqueline Diramio
(74) *Attorney, Agent, or Firm*—Ferdinand M. Romano, Esq.; Beusse Wolter Sanks Mora & Maire, P.A.

(57) ABSTRACT

A rapid assay concentration device. In one form, the device includes a substrate and a plurality of elongated membranes on the substrate. At least one capture zone is formed in each membrane. Each capture zone is responsive to the presence of a target chemical in the fluid. Capture zones on different membranes have different threshold levels of response to the chemical. In a method for monitoring temporal changes of analyte levels in a source multiple test devices are provided, with each device including a plurality of regions. Each region is responsive at a different sensitivity level to indicate presence of the analyte. A source sample is brought into contact with a first of the test devices to determine whether the source contains a level of analyte sufficient to induce a response thereto in one or more of the test unit regions. A different sample from the source is brought into contact with a second of the test devices to determine whether the source contains a level of analyte sufficient to induce a response thereto in one or more regions of the second test device.

14 Claims, 5 Drawing Sheets

U.S. PATENT DOCUMENTS

| | | | | |
|---|---|---|---|---|
| 4,042,329 A * | 8/1977 | Hochstrasser | ............... | 436/71 |
| 4,059,407 A * | 11/1977 | Hochstrasser | ............... | 422/56 |
| 4,904,605 A * | 2/1990 | O'Brien et al. | ............. | 436/169 |
| 5,710,372 A * | 1/1998 | Becket | ..................... | 73/53.01 |
| 6,203,757 B1 | 3/2001 | Lu et al. | | |
| 6,403,380 B1 * | 6/2002 | Catt et al. | .................... | 436/65 |
| 6,656,745 B1 * | 12/2003 | Cole | ......................... | 436/514 |
| 2003/0124737 A1 * | 7/2003 | O'Connor et al. | ........... | 436/510 |
| 2003/0175992 A1 * | 9/2003 | Toranto et al. | .............. | 436/514 |
| 2004/0096985 A1 * | 5/2004 | Kenjyou et al. | ............. | 436/514 |
| 2005/0136490 A1 * | 6/2005 | Rutanen | .................... | 435/7.2 |
| 2006/0019404 A1 * | 1/2006 | Blatt et al. | .................. | 436/169 |

\* cited by examiner

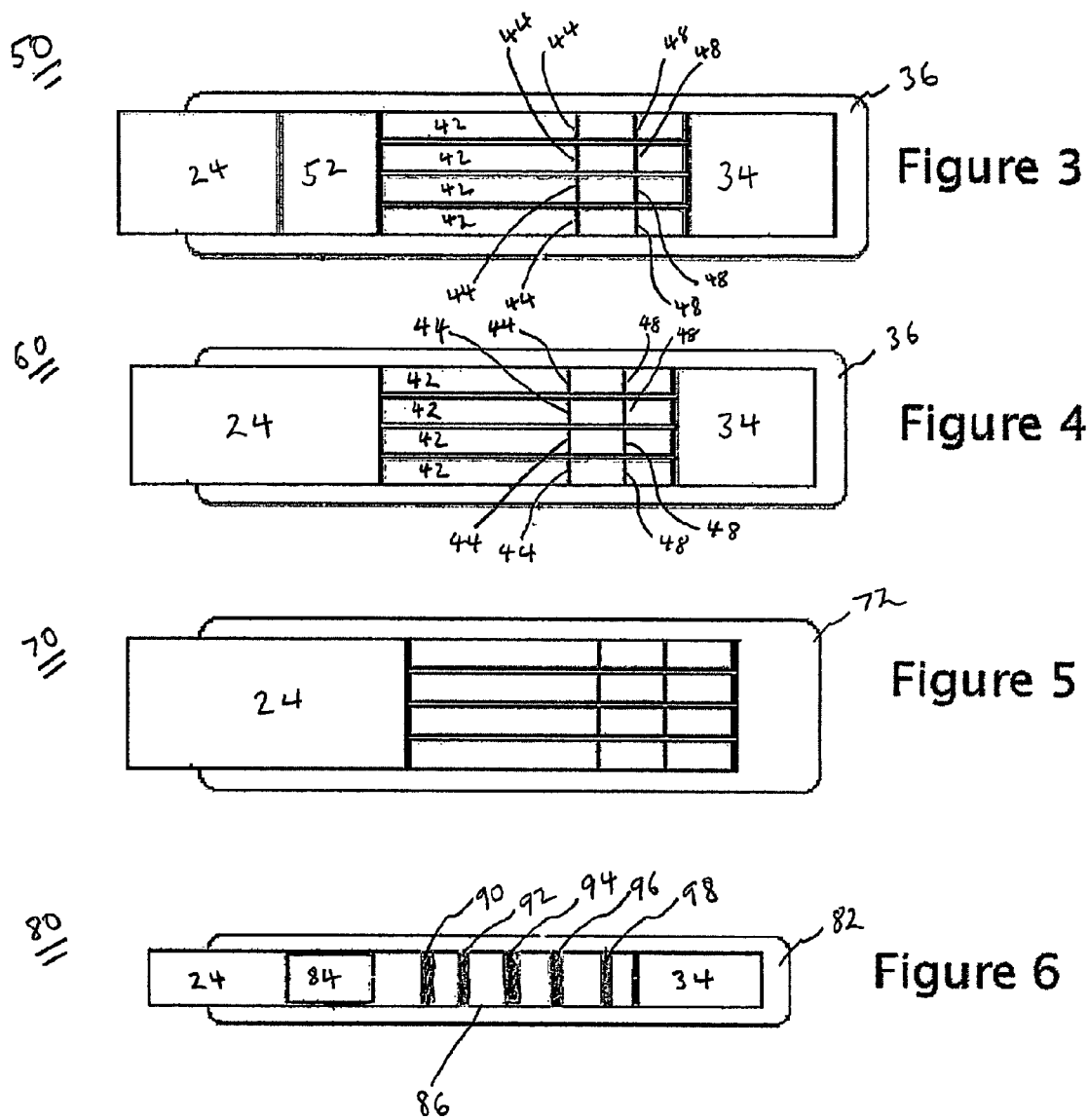

| Testing Day | Result |
|---|---|
| 1 | Level 1 + |
| 3 | Level 2 + |
| 5 | Level 1 + |
| 6 | Negative |

Figure 12E

| Testing Day | Result |
|---|---|
| 1 | Level 1 + |
| 3 | Level 3 + |
| 4 | Level 4 + |

Figure 12D

| Testing Day | Result |
|---|---|
| 1 | Level 1 + |
| 3 | Level 1 + |
| 4 | Level 1 + |
| 5 | Level 1 + |
| 6 | Level 1 + |

Figure 12C

| Testing Day | Result |
|---|---|
| 1 | Level 1 + |
| 3 | Level 1 + |
| 4 | Level 2 + |
| 5 | Level 2 + |
| 6 | Level 3 + |
| 7 | Level 3 + |

Figure 12B

| Testing Day | Result |
|---|---|
| 1 | Level 1 + |
| 3 | Level 2 + |
| 5 | Level 3 + |
| 7 | Level 4 + |

Figure 12A

PORTABLE DIAGNOSTIC DEVICE AND METHOD FOR DETERMINING TEMPORAL VARIATIONS IN CONCENTRATIONS

CROSS REFERENCES TO RELATED APPLICATIONS

This patent application claims priority to and the benefit of the provisional patent application filed on Oct. 8, 2002, and assigned Ser. No. 60/416,676.

BACKGROUND OF THE INVENTION

1. Field of the Invention

This invention relates to monitoring changes in chemical levels and, more specifically, to methods and devices for determining such changes. By way of example, the invention may be used to monitor temporal changes of analyte levels in a source.

2. Description of the Related Art

Tracking of variable concentrations in, for example, fluids, is important for monitoring the status of physical, biochemical and biological systems. Such monitoring is useful to assess health, environmental conditions and medical concerns. Generally, it is desirable to monitor concentrations to identify trends indicative of certain conditions. For example, prompt awareness of an adverse condition is often essential to enable timely intervention. This is critically important when life and health are in jeopardy.

In the past, systems and methodologies for assessing chemical conditions, e.g., based on concentrations of representative species, have included conventional laboratory analyses and, to a lesser extent, portable assay methodologies. Assay methodologies are relatively complex and normally require analytical or quantitative procedures in order to observe features indicative of a desirable or undesirable condition. Accordingly, at least limited training is needed because the procedures entail, for example, mixing of fluids in predetermined proportions. Common examples of such procedures include analyses of water to determine whether concentrations of certain constituents, e.g., toxins in drinking water, have exceeded safe limits, or whether certain other constituents, e.g., swimming pool chemicals, have fallen below recommended levels.

While it is desirable to provide simplified assay procedures for a wide range of assessments, relatively few methods of performing an analysis have been found suitable for monitoring of chemical concentrations by non-specialists. It is especially desirable to provide simplified analysis procedures in the fields of environmental protection, health monitoring and medical diagnosis. The value of providing such procedures is evidenced by the disadvantages present in contemporary methodologies. Consider, for example, the medical field, wherein determination of chemical concentrations, such as hormone levels, may be indicative of disease or another medical concern. Typically, these types of quantitative assays require time-intensive laboratory analysis of blood or another body fluid.

A well-known case in point is the assessment required to confirm a healthy pregnancy. To effect that assessment, blood levels of chorionic gonadotrophin (commonly referred to as hCG) must be periodically monitored to confirm that hCG levels are rising rapidly during the first trimester of pregnancy. In particular, during the progression of a normal pregnancy, early hCG levels will typically double every two to three days. Studies show that among 85% of normal pregnancies such doubling occurs at least every 72 hours. Observation of this doubling is commonly used as an indication of a healthy pregnancy. On the other hand, in those circumstances when a consistent increase in the hCG level is not observed, there is a correlation with miscarriages or ectopic pregnancies.

A generally accepted method of monitoring temporal shifts in hCG levels requires a series of serum beta hCG quantitative tests. Typically, a Solid Phase Enzyme Linked Immunosorbent Assay (ELISA) is performed at designated time intervals to monitor changes in hCG concentration. Each ELISA test requires adding serum to an hCG antibody microtiter well. If hCG is present, it will bind to the antibody in the well. When another antibody, i.e., a label, is added it binds to the antibody-antigen complex. This labeling allows for development into a colored complex. This color is then analyzed spectrophotometrically such that the hCG concentration can be determined by the color intensity in order to indicate quantitative shifts in levels of hCG. The test is in common use because a measured decrease in the hCG level may be an early warning sign of a pregnancy complication.

While ELISA test results are highly accurate, the series of ELISA tests cannot be performed in a home environment or by an unskilled person. Rather, they require a laboratory analysis performed by trained technicians and, normally, a physician's approval. Further, the patient must make multiple visits to have the blood drawn. The results for each ELISA test will usually take at least 24 hours, necessitating an undesirable delay in obtaining important results. In addition, the time-consuming nature of the laboratory analysis renders this type of testing very expensive. Examples of ELISA tests for pregnancy are described in U.S. Pat. Nos. 5,198,366 and 5,182,216, each incorporated herein by reference.

Another example of periodic monitoring of an analyte level in a human sample is the routine screening for Prostate Specific Antigen, PSA. The level of PSA in a man's blood generally increases with age. However, a sudden or rapid rise, particularly in males with increased risk factors, may be an early warning sign of cancerous development within the prostate gland. Also, a slowly increasing level of PSA over time can also be indicative of potentially cancerous growth.

The American Cancer Society recommends that all men over the age of 50 be routinely screened by their doctor for any signs of prostate cancer. The PSA test is a blood test performed by a doctor that will give a quantitative determination of PSA level in the blood. A normal PSA level for the average man ranges from 0 to 4 ng/mL, while levels from 4 to 10 ng/mL are slightly elevated, and anything above 10 ng/mL can be considered abnormally elevated. During an annual physical, a man may opt to have the PSA test performed. If the results of the test show moderate levels, the man will generally not be retested further, at least until the next annual physical. The lengthy time period in between tests may be of concern for certain men with high risk factors. Additionally, in that time period, a sudden rapid rise may occur, but would not be apparent without more frequent testing.

SUMMARY OF THE INVENTION

According to several aspects of the present invention, simplified assessment procedures and analysis systems suitable for use by lay persons are made available. Heretofore, test procedures for assessing concentration have not reached a level of simplicity suitable for use by unskilled persons. Nor have they reached a level of reliability such that one could place a high level of confidence in the results. Specifically, with regard to monitoring hCG levels, rapid and reliable screening tests for confirming the normal status of a pregnancy have not been available. It is desirable to apply test procedures and systems in the form of home use tests to monitor changes in analyte levels such as hCG and PSA.

Provision of simplified test procedures and associated assay systems as disclosed herein are indicative of concentrations of representative chemical species. These render the tasks of monitoring and assessing conditions quick, reliable and suitable for use by persons without specialized training and without requiring the selection or measurement of chemicals to effect the assay.

In one form of the invention a method is provided for monitoring temporal changes of analyte levels in a source. Multiple test devices are provided, with each device including a plurality of regions. Each region is responsive at a different sensitivity level to indicate presence of the analyte in the source. A sample from the source is brought into contact with a first of the test devices to determine whether the source contains a level of analyte sufficient to induce a response thereto in one or more of the test unit regions. Subsequently, a different sample is obtained from the source and brought into contact with a second of the test devices to determine whether the source contains a level of analyte sufficient to induce a response thereto in one or more regions of the second test device. The responses can provide information about temporal changes in analyte concentration.

A rapid assay concentration device is also provided. In one form, the device includes a substrate and a plurality of elongated membranes positioned on the substrate. The membranes are of the type which exhibit capillary flow of fluid therethrough. At least one capture zone is formed in each membrane. Each capture zone is responsive to the presence of a target chemical in the fluid. Capture zones on different membranes have different threshold levels of response to the chemical.

A test device according to the invention may include plurality of distinguishable regions each positioned on the substrate and coupled to receive a portion of the sample, each region capable of generating a visually discernable signal in response to a minimum level of analyte in the sample.

In another embodiment of the invention a rapid assay concentration device includes a substrate and an elongated test membrane having multiple spaced-apart capture zones formed thereon, each positioned to provide a different sensitivity response to the presence of analyte in the source.

In another method for monitoring changes in analyte level in a source, multiple measurably distinguishable sensitivity levels are defined with each indicative of a different amount of analyte in the source. A first test device is provided which includes a first region thereon responsive to the presence of analyte in the source at a first of the sensitivity levels. A second test unit is provided which includes a first region thereon responsive to the presence of analyte in the source at a second of the sensitivity levels. A first sample from the source is brought into contact with the first unit to provide the first region thereon an opportunity to indicate presence of analyte in the sample at at least the first level. A second sample from the source is brought into contact with the second unit to provide the first region thereon an opportunity to indicate presence of analyte in the sample at at least the second level.

BRIEF DESCRIPTION OF THE FIGURES

The foregoing and other features of the invention will be apparent from the following more detailed description of the invention when read in conjunction with the accompanying drawings, in which:

FIG. 3 illustrates in plan view a second embodiment of the invention;

FIG. 4 illustrates in plan view a third embodiment of the invention;

FIG. 5 illustrates in plan view a fourth embodiment of the invention;

FIG. 6 illustrates in plan view a fifth embodiment of the invention;

FIG. 12 illustrates combinations of sequential test sequence and results for one application of the invention.

Like reference characters refer to the same or similar parts throughout the different figures. The drawings are not necessarily to scale, emphasis instead being placed upon illustrating the principles of the invention.

DETAILED DESCRIPTION OF THE INVENTION

Figure 1:
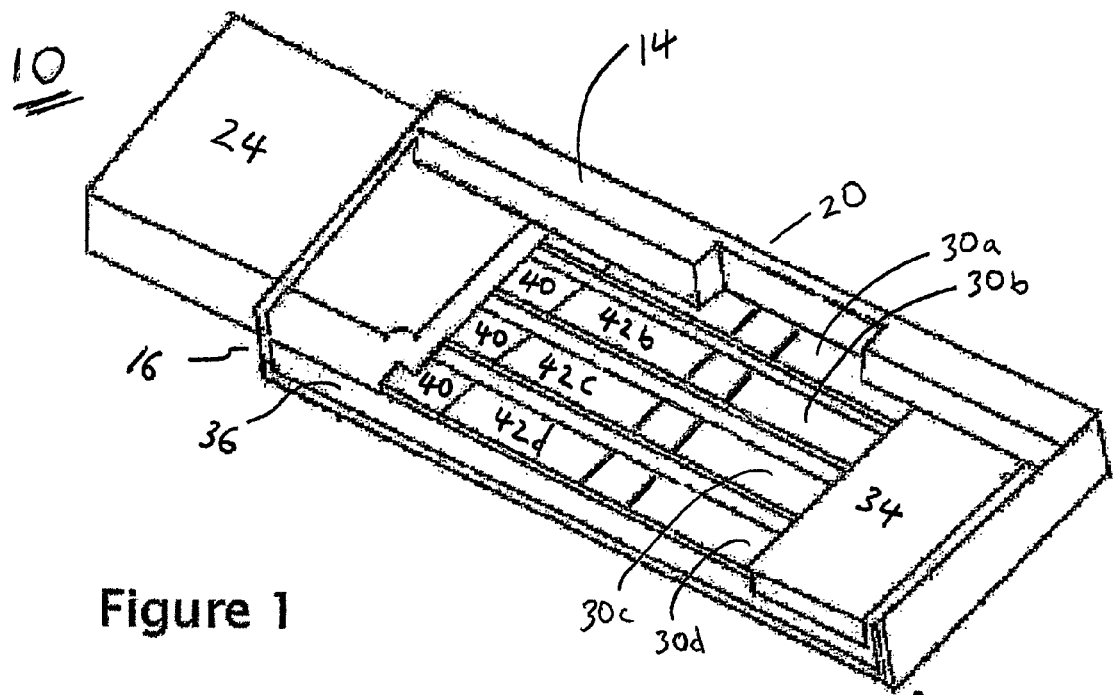
FIG. 1 illustrated in perspective view a device according to the invention.

Before describing in detail particular features of the invention it should be noted that the present invention provides a novel combination of elements and method steps. Accordingly, the drawings primarily show specific details pertinent to the present invention so as to not obscure the disclosure with technical details that will be readily apparent to those skilled in the art having the benefit of this description.

Although the embodiments of the invention now described have specific application to the monitoring of changes in hCG levels, the concepts disclosed are readily applicable to monitoring of temporal changes in concentration for a wide variety of chemicals present in an arbitrary source. It is also noted that, although formation of an immunocomplex is disclosed as a means for indicating presence of the targeted species within one of multiple test ranges, other ligand recognition systems will be suitable depending on the chemicals involved and specific test goals. Detection is commonly, but not exclusively, effected by, first, the association of a detector reagent with a capture reagent, typically in a membrane. The reagents may be synthetic constructs or may be derived from natural sources.

Numerous means of detecting the presence of hCG commonly used in home pregnancy tests to determine the mere presence or absence of the hormone. With regard to the monitoring of hCG levels, i.e., concentrations, one methodology according to the invention is based in part on a well known technique for detecting the presence of hCG. This methodology begins with allowing the source sample to begin a lateral flow through a fibrous medium to a first zone formed of porous material (commonly termed a conjugate pad area). The first zone contains an appropriate labelled detector reagent. Interaction between the detector reagent and target species present in the source sample results in an association between the two molecules. Subsequently this antigen-antibody complex is carried by the source sample to a second zone, formed on a membrane and referred to as a testing area Flow through the membrane is essentially lateral and unidirectional. Conventionally, a predefined region along the surface of the testing area, referred to as the capture zone contains a species of immobile antibodies which also associate with the target species in the antigen-antibody complex to form an antigen-antibody-antigen complex.

Once formed, this sandwich complex remains in a relatively a stable position within the capture zone. When a sufficient number of sandwich complexes are formed in the capture zone, their presence in the capture zone is visually detectable. With a sufficient quantity of sandwich complexes present in the capture zone, it is possible to visually determine whether some threshold concentration of the target species, hCG, is present in the source sample. The ability to detect the mere presence of the target species in the sample is dependent on the sensitivity of the control zone to develop a detectable signal in response to the presence of the analyte. In the examples described, the signal is visually detectable, but, more generally, the capture zone may produce any kind of detectable signal.

Preferably, when applying this method to monitor levels of analyte, the reagents and other components are provided in a manner such that sensitivities have minimal variations. This assures consistent and repeatable determinations among concentration ranges in the monitoring process.

A control antigen may be provided in the fibrous medium. This antigen is selected to be inert with respect to the antibodies deployed to form complexes with the target species, e.g., hCG. The control antigen is allowed to be carried by the source sample through the first membrane zone, through the testing area and past the capture zone to a separate and distinct control zone containing a second immobile antibody species embedded therein. The second immobile species readily forms an antigen-antibody complex with the control antigen. The control antigen and second antibody species are provided in sufficient quantities that when combined they result in a visually discernable line or mark in the control zone.

Discussions regarding the lateral flow technique tests and immunochromatographic assays are found in the following U.S. Patents, each of which is now incorporated herein by reference: U.S. Pat. Nos. 6,607,922; 6,541,277; 6,027,943; 5,354,692; 5,654,162; 5,591,645; 5,145,789; 5,591,645; 5,798,273; 5,622,871; 5,602,040; 5,714,389; 5,879,951; 4,632,901; and 5,958,790.

Figure 2A:
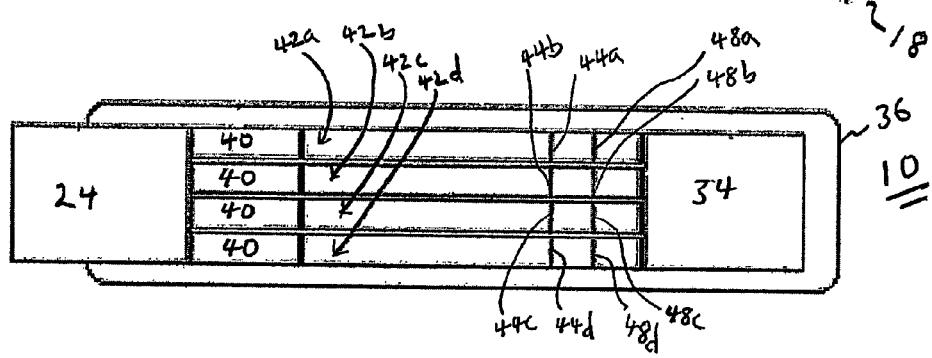
FIG. 2A provides a plan view of the FIG. 1 device.

FIGS. 1 and 2A illustrate an exemplary rapid assay concentration device 10 capable of indicating whether a target analyte is present in a source sample at a level within one of several possible ranges. Typically, the level will correlate with a concentration range, in which case the device 10 as well as other embodiments of the invention provide a fast means for determining a chemical concentration by simply wetting a region of the device with a sample and then observing a visible change along one or more assay regions according to, for example, an immunologic reaction.

Several of the devices 10 may each be used on a different day to assay for the hormone hCG and, as more fully explained herein, the device 10 provides a quick and easy means for determining the hCG concentration such that the assay may be conducted by a nonspecialist according to simple package instructions. That is, by monitoring whether temporal changes in concentration of hCG in urine follow a typical pattern, a woman may independently assess whether her pregnancy is following a healthy progression during the first trimester.

More generally, multiple devices constructed according to the invention may be used sequentially to monitor temporal changes in a variety of analyte levels by examining samples taken from a source at different points in time. For purposes of illustration, methods are described for performing exemplary tests with the device 10.

Preferably, the device 10 includes a housing 14 about which other components are placed. The housing as illustrated in FIG. 1 may be formed of molded plastic although other common materials may also be used to form the housing, including porous or fibrous products, e.g., cardboard, and such materials may be coated or otherwise treated to reduce permeability to water-based fluids.

The housing 14 is of an elongated shape, having first and second opposing end portions 16 and 18 and a mid region 20. A sample region 24 is located about the first end portion 16 and multiple distinct assay regions 30 are positioned in the mid region 20. As described herein each assay region includes a conjugate pad and a test membrane which contains a capture zone and a control zone. Four such assay regions 30, are individually identified by the reference numbers 30a, 30b, 30c and 30d. An optional liquid absorbing medium 34 is positioned within the housing 14 near the second end portion 18. When a fluid source sample is provided to the sample region 24 the sample migrates into the assay regions 30 and portions of the sample move beyond the assay regions 30 to reach the liquid absorbing medium 34. To facilitate ease of assembly the sample region 24, the assay regions 30 and the absorbing medium 34 are mounted on a substrate 36, e.g., with an adhesive, prior to positioning these components in the housing 14. The substrate may be formed of a plastic or laminated cardboard.

The overall length of the device 10, from the first end portion 16 to the second end portion 18, may be less than 20 cm, preferably between 10 and 13 cm. The sample region 24 extends away from the housing 14 to enable conventional mid-stream urine sampling, adding up to 5 cm to the overall device length. In this and other illustrated embodiments, the function of the sample area is to receive the sample, e.g., urine, and facilitate even and controlled movement of the sample to the assay regions 30.

The sample region 24 may comprise a woven mesh or cellulose filaments. Alternately, a mesh may be formed with glass fibers, polyurethane, polyacetate or cellulose acetate. The matrix which forms the region 24 may be coated or otherwise modified with materials that (i) accelerate movement of the sample fluid; (ii) enhance solubility of the detector reagent; or (iii) allow for a control indicator line to form in a control zone on the assay regions. By way of example and not limitation, components which can be added to the matrix of the sample region include: proteins, detergents, surfactants and buffer salts.

To provide a control indicator, a complex protein or other compound that is relatively inert to the target species is placed in the sample region 24 to serve as the control antigen. For example, the control antigen may be mouse immunoglobin. Alternately the control antigen may be added to the conjugate pads.

FIG. 2A provides a plan view of the device 10 without the housing shown in order to further illustrate the assay regions 30 in relation to the sample region 24 and the absorbing medium 34. As noted above, the assay regions 30 each include a conjugate pad 40 containing a detector reagent specific to hCG. Adjacent each conjugate pad 40 is a test membrane 42 comprising a capture zone 44 and a control zone 48. For clarity the test membranes, capture zones and control zones of each assay region are individually designated as test membranes 42a, 42b, 42c and 42d, capture zones 44a, 44b, 44c, 44d and control zones 48a, 48b, 48c and 48d.

Preferably, as shown in FIG. 1, the test membranes are positioned in spaced-apart relation to one another in order to prevent movement of source sample between membranes. Alternately the membranes may be brought close together to create a more compact device by isolating them, one from another, with a fluid impermeable film such as mylar. In other embodiments the housing can be configured to provide fluid isolation walls between which each of the membranes may be deposited. Surface portions of the test membranes may also be sealed such that fluid can only enter and exit the membranes at the opposing ends that are in fluid communication with the conjugate pad 40 and liquid absorbing medium 34.

The capture zones 44 contain an immobile antibody (capture reagent) specific to hCG. Preferably, on each test membrane 42, the control zone 48 is positioned adjacent a capture zone 44 on the side of the capture zone farthest away from the associated pad 40 so that the control zone receives flow of fluid from a source sample after the fluid has passed through the adjacent capture zone 44. The control zones 48 contain a capture reagent specific to the presence of the control antigen but not responsive to hCG.

The detector reagent provided in the conjugate pad 40 may be of a common format such as the type formed with colored latex beads or colloidal gold particles having conjugating antibodies attached thereto. The antibody component may be a monoclonal or polyclonal anti-hCG antibody or another hCG ligand. Generally, the detector reagent may also be formed with enzyme conjugates, other colloidal metals, nonmetal sol, dye or pigment, or fluorescent or magnetic particles.

When analyte present in the source sample comes into contact with each conjugate pad 40, detector reagent present therein forms labeled antibody-antigen complexes with the analyte, which migrate to the capture zones. In the past conjugate pads have been applied, e.g., in home pregnancy test kits, in a manner which merely assured uniform transfer rate of liquid through the conjugate pad to a test membrane. A feature of the present invention is that a different conjugate pad 40 may be provided for each test membrane and, according to one embodiment, the pads 40 may be designed to effect different flow rates of source sample in their respective assay regions 30. When the source sample moves through different ones of the conjugate pads 40 at differing rates, immobilized reagent in each test membrane will experience a different effective concentration of analyte with which to solubilize. Variables of the pads 40 which may be modified to adjust flow rates include porosity, cross sectional flow area and length of pad through which the sample flows.

Properties of the test membranes 42 also influence analyte sensitivity. By adjusting either or both the conjugate pad properties and the test membrane properties, a measurably different analyte sensitivity can be established in each of the capture zones. With this variable sensitivity the visually detectable response of each to the analyte will be a function of a different threshold concentration of analyte in the sample.

The test membranes are commonly made from polymers, including nitrocellulose, polyvinylidine fluoride, nylon and polyethersulfone. Sensitivity of the test membranes to different analyte concentrations is a function of numerous variables, in many instances based on changes in actual flow rate of the analyte or the detector. Variations in these flow rates influence the ability of immobile antibodies in the capture zones 44 to form complexes with the analyte species.

In this example embodiment the capture zones may be regarded as an ordered array based on sensitivity for detecting analyte. That is, the zone 44a on the membrane 42a is the most sensitive of the four capture zones 44a, 44b, 44c and 44d, providing a visually detectable response for the lowest threshold analyte concentration detectable by the device 10. When comparing adjacent zones beginning with zone 44a, the sensitivity of each of the zones 44b, 44c and 44d is progressively lower than the prior zone in the array, such that each only provides a visually detectable response at a progressively higher threshold level of analyte concentration in the sample. Accordingly, zone 44d only provides a response for the range of concentration having the highest threshold analyte concentration detectable by the device 10. Thus, a feature of the invention is that each of the capture zones will vary in sensitivity to the analyte. Each assay region 30 may be designed to require that a different minimum concentration of analyte be present in the sample in order for a positive result to appear.

The absorbing medium 34 is in contact with the assay regions 30 to draw source sample through the test membranes 42 to increase the amount of sample that flows completely through the assay regions 30. The absorbing medium 34 may be formed of woven or cellulose fibers.

There are many techniques for varying sensitivity of the assay regions 30. For example, increases in membrane porosity will increase the source sample flow rate through the membrane. Other means for varying sensitivity level for detecting the analyte include selecting different membrane thicknesses, varying parameters of the capture zone or the amount of capture reagent present in the capture zone 44.

Although design and operation of the invention are not limited to any one theory or mechanism, one basis upon which devices according the to the invention may be designed relates to porosity of the test membranes 42. Given a unidimensional lateral flow through the membranes, the faster the movement of analyte through the capture zone, the less time there is for the complexes to form. Accordingly, membranes with low porosities will detect low levels of analyte concentration while membranes with higher porosities will only detect higher levels of analyte concentration.

Consistent with the lateral flow technique, increasing porosity of the membrane will result in increased capillary flow rate. Because lateral flow is, by design, essentially unidirectional through the membranes 42, the faster that the analyte passes through the capture zones, the less time the capture antibodies present in the capture zone will have to form a complex with the analyte. Therefore, a membrane of higher porosity will be less sensitive.

The effective sensitivity of a membrane is inversely proportional to the square of the flow rate. Therefore, if the capillary flow time through the test membrane 42a is X and the capillary flow time through the test membrane 42b is 2X the ratio of sensitivities between the membranes 42a and 42b is 0.25. Thus the device 10, as well as other embodiments of the invention having multiple, distinct test membranes, can provide multiple ranges of sensitivity to a target analyte according to porosity characteristics of each test membrane.

Suitable membranes are commercially available. One source, Millepore Corporation, Billerica, Ma. U.S.A. manufactures a series of membranes having characteristics that serve to illustrate the principles of the invention. Four such membranes could be arranged in the device 10 to provide capture zones having progressive sensitivity thresholds that approximately double from one capture zone to the next in the array.

For a membrane having dimensions of 1 cm by 1 cm by 0.014 cm (a total volume of 0.014 $cm^3$ or 14 uL) and a 70 percent porosity, the open volume within the structure is 9.8 uL. Capillary flow rate can be changed by changing the porosity of the membrane. The less time that the antibody-antigen complex has to react with the antibody in the capture zone, the lower the sensitivity. This concept can be used to design the sensitivities of all membranes 42 on the test device 10.

For example, the Millipore membrane model HF240 has a capillary flow time of 240 sec/4 cm while the Millipore membrane model HF180 has a capillary flow time of 180 sec/4 cm. With all other factors being equivalent, the model HF180 is theoretically 56 percent or about half as sensitive to analyte detection as the model HF240.

The Millipore model HF120 membrane (having a capillary flow time of 120 sec/4 cm) would theoretically provide 44 percent or about half the sensitivity as that of the model HF180, and theoretically 25 percent or one fourth the sensitivity as that of the model 240.

The Millipore model HF90 membrane (having a capillary flow time of 90 sec/4 cm) is theoretically about 56 percent or, again, about half as sensitive to analyte detection as the model HF120, 25 percent as sensitive as the model HF180 and slightly more than one eighth as sensitive as the model HF240.

These four membranes (Millipore models HF240, HF180, HF120 and HF90) could, in sequence of decreasing sensitivity, be positioned to provide the ordered array of test membranes [42a, 42b, 42c, 42d]. With this arrangement the array of capture zones [44a, 44b, 44c, 44d] will display positive results based on four threshold sensitivities, e.g., 100 mIU/mL, 200 mIU/mL, 400 mIU/mL and 800 mIU/mL. The absolute levels of sensitivity (i.e., a measure of concentration) could be calibrated into the device based on empirical data, and the threshold sensitivities of the device could be adjusted by modifying other sensitivity parameters such as the amounts of detector reagent and capture reagent in the assay regions.

Minor sensitivity adjustments could be made to further calibrate the threshold levels of response in each capture zone by modifying flow rates from associated conjugate pads, by modifying the amount of detector reagent or the amount of capture reagent in each assay region relative to the other assay regions.

Figure 2B:
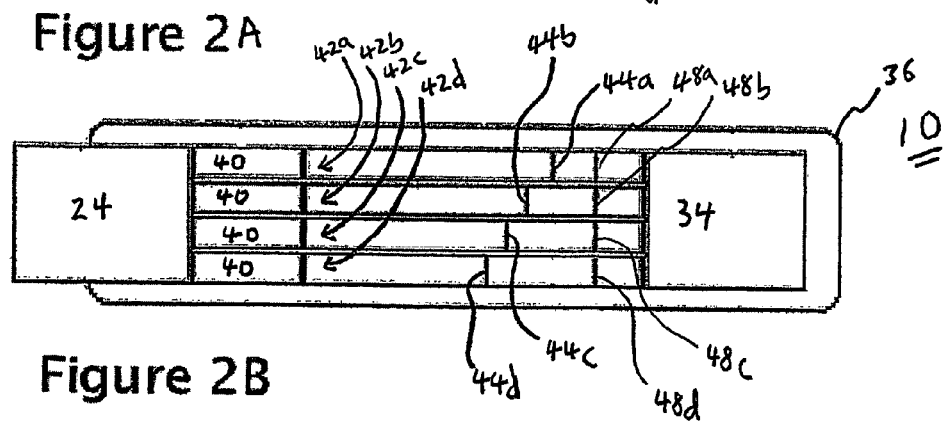
FIG. 2B provides a plan view of the FIG. 1 device, illustrating an alternate feature thereof.

Further, to facilitate visual analysis, the flow dynamics and capture zone responsiveness of each test membrane can be modified such that adjacent capture zones in the array may be spatially staggered with respect to one another. See, for example, FIG. 2B wherein the most sensitive capture zone 44a is closest to the liquid absorbing region 34 and each next zone in the ordered array is positioned farther from the liquid absorbing region 34 such that the zone 44d is farthest from the liquid absorbing region 34 and closest to the sample region 24. The staggered arrangement can facilitate visual interpretation of the display as it is determined which capture zone best correlates with the actual analyte concentration, i.e., the capture zone of highest threshold concentration range for which there is a visually detectable response. This configuration may be created in accord with the principles of capillary flow, as described herein with regard to the device 80 of FIG. 6. The capture zone sensitivities are a function of the distance relationship between the sample region and each capture zone, allowing the capture zones in different membranes to form a staggered relationship. In such cases the relative sensitivities of the several test membranes may be further adjusted by changing the cross sectional area of the conjugate pads, varying membrane porosity, or modifying detector concentrations to achieve the desired result.

To more clearly present features of the invention, other devices are also shown in the figures without illustrating the optional housing 14. The device 50, a first alternate embodiment of the invention shown in FIG. 3, differs from the embodiment of FIGS. 1 and 2 in that multiple conjugate pads 40 are not present. Rather, one conjugate pad 52 is positioned in contact with the sample region 24 and the test membrane 42 of each assay region 30 to transfer portions of the source sample to each of the capture zones 44. Because the labeled antibody reagent (specific to the analyte) is introduced to the source sample in the conjugate pad 52, the amount of labeled antibody reagent that is received by the sample will be the same for each portion of the source sample that enters a different test membrane 42. For this embodiment desired variations in the sensitivity among each of the separate capture zones can be effected by, for example, changing membrane characteristics such as porosity and thickness.

Another embodiment is shown in FIG. 4. A device 60 is also similar to the device 10 except that it does not include any conjugate pad. In this design all of the detector reagents are provided in the sample region 24. Each of the test membranes 42 physically contacts the sample region 24 to receive source sample with detector reagent flowing therewith.

The device 70 shown in FIG. 5 is a more simplified system for determining analyte concentration. It comprises a sample region 24 and multiple test membranes all formed on a substrate 72. The substrate 72 may be a cellulose product. No conjugate pad and no absorbing medium are present. Alternately the device could include one or four conjugate pads configured as described for the embodiments of FIGS. 1 and 3.

Another rapid assay concentration device 80 is illustrated in FIG. 6. The device may be placed in a housing of the type illustrated in FIG. 1, but is shown mounted on a plane substrate or backing 82 in the plan view of FIG. 6. The device 80 includes a sample region 24 for midstream testing and a conjugate pad 84 containing detector reagent. The conjugate pad 84 is similar in structure to the pad 40 described in FIGS. 1 and 2. The pad 84 is positioned for receiving source sample from the region 24 and transmitting both the detector reagent and the source sample to a single elongate test membrane 86. Preferably, a liquid absorbing medium 34 is positioned to receive source sample flowing from the test membrane 86. As described with respect to the devices shown in FIGS. 4 and 5, the device 80 may function without the conjugate pad 84 or the liquid absorbing medium 34. However, the medium 34 assures a consistent lateral flow of the source sample according to which capture zones 90, 92, 94 and 96 may be positioned in a calibrated manner. A control zone 98, independent of the capture zones, is positioned closer to the absorbing medium 34 than the capture zones.

The relationship for the spacing of capture zones along the test membrane and with respect to one another is based on the principle that capillary flow rate decreases exponentially as the distance traveled through the membrane 86 increases. So, for example, the time required to double a distance already traveled takes twice as long as the time taken to travel the original distance. The farther along the test membrane that a capture zone is located, the slower the flow rate of the analyte through that zone. The longer that portions of the flowing fluid are in contact with the capture zone, the greater the number of captured antigen-antibody complexes. Thus, the farther along the testing membrane that a capture zone is positioned, the more responsive will the zone be to the presence of low analyte concentrations.

Assuming substantially the same concentration of capture reagent is placed in each capture zone, then any plurality of capture zones positioned along the same membrane can provide a detector series of progressively greater sensitivity. The capture zones may be spaced in a desired manner to create desired threshold values each indicative of a different minimum analyte concentration.

Figure 7:
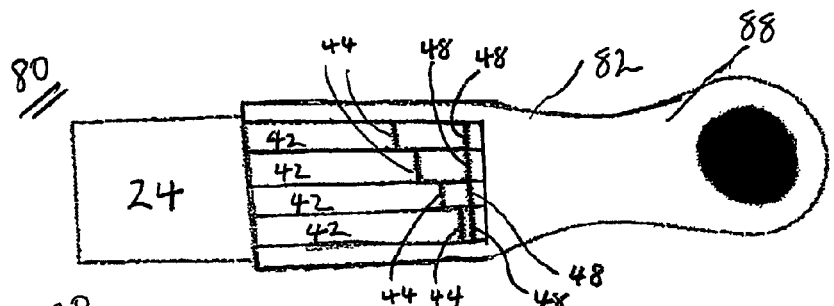
FIG. 7 illustrates in plan view still another embodiment of the invention.

FIG. 7 illustrates a simplified mid stream rapid assay concentration device for analyzing analyte concentration in urine. The device 80 comprises an elongated backing 82 to support the testing device areas which include a sample region 24 in contact with multiple test membranes 42 of the type described with reference to FIGS. 2A and 2B such that a source sample will freely flow from the sample region 24 to the capture zones 44 and control zones 48 formed thereon. The sample region 24 is positioned at one end of the backing 82 and the opposing end of the backing 82 provides a handle region 88 for the user to hold while wetting the region 24 with the source sample. Individual conjugate pads of the type shown in FIG. 2 (not shown) may be positioned between the sample region 24 and the test membranes 42, or a single conjugate pad of the type shown in FIG. 3 may be positioned between the sample region 24 and the test membranes 42. A liquid absorbing medium 34 may be placed on the handle region in contact with the test membranes 42 to facilitate rapid, unidirectional flow of the sample from the sample region 24 and through each of the test membranes 42.

The overall length of each of the devices 10, 50, 60, 70 and 80 may range from approximately 10 cm up to about 20 cm or more. For the device 80 the length is measured from an edge of the sample region 24 to the end of the handle region 88. The widths of each of the devices 10, 50, 60, 70 and 80 is primarily a function of the test membrane width. With four test membranes 42, as shown in FIGS. 2, 3, 4, 5 and 7, the width of the device 80 may be on the order of four to five cm or more, but preferably is less than 3 cm. The devices could have more or fewer assay regions than shown in the figures. The width of the device 80, having one test membranes may be up to approximately 2 cm but could be substantially smaller.

Figures 8A, 8C:
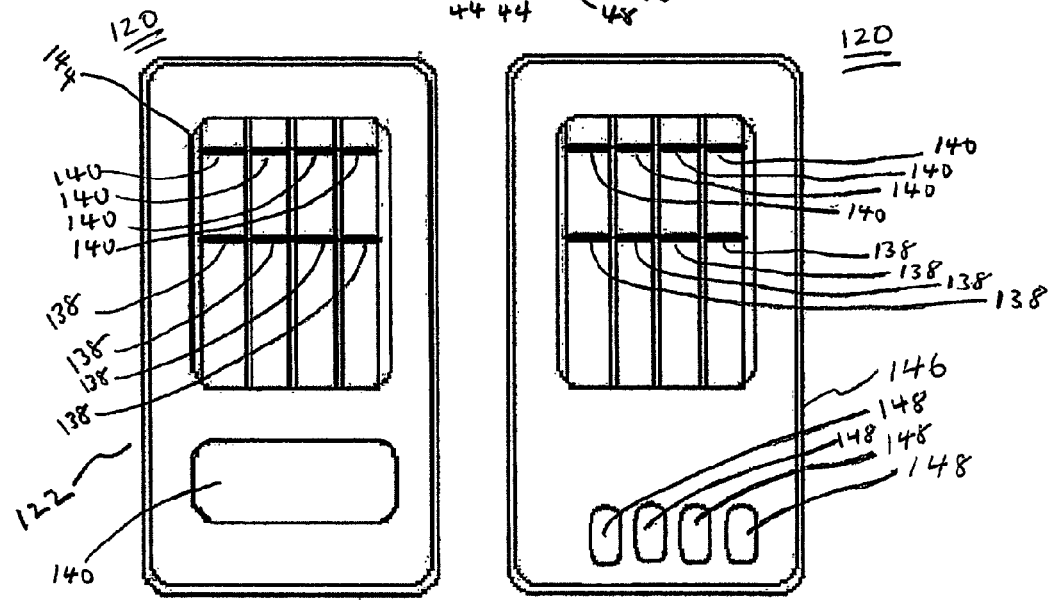
FIGS. 8A, 8B and 8C illustrate features of the invention as may be embodied in a cassette design.
Figure 8B:
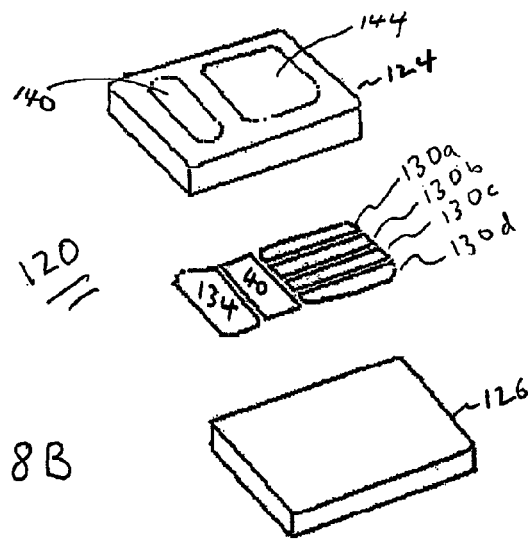

A device 120 shown in the plan view of FIG. 8A and the exploded side view of FIG. 8B is similar in function to each of the aforedescribed devices 10, 50, 60, 70 and 80, but is formed in a cassette style. A plastic casing 122 has mating upper and lower portions 124 and 126 between which a series of test membranes 130 are positioned. The test membranes 130 are individually designated 130a, 130b, 130c and 130d. The membranes 130 are positioned between a sample region 134 and a liquid absorbing medium (not illustrated) to effect flow of a source sample therethrough. One or more conjugate pads may be interposed between the sample region 134 and the series of test membranes with the detector reagent provided therein as described with respect to the device 10 of FIG. 2 and the device 50 of FIG. 3. Otherwise, the detector reagent may be placed in the sample region 134. Each of the test membranes 130 includes a capture zone 138 and a control zone 140 formed therein as described for the capture zones 44 and control zones 48 of the device 10. The capture zones of adjacent membranes 130 may or may not be staggered with respect to one another. Preferably the least sensitive capture zone is on membrane 130a.

As shown in FIGS. 8A and 8B, the upper casing portion 124 includes a sample opening 140 which exposes the sample region in order to receive the source sample. The sample may be placed in the opening 140 with a dropper or otherwise. The upper casing portion 124 also includes a window opening 144 exposing portions of each membrane 130 such that the surface areas over which each associated capture zone 138 and control zone 140 are formed may be observed. Thus when capture zones develop visually detectable responses to the analyte the responses are readily shown as a series of lines in the window opening 144. As confirmation that the device 120 is functioning properly, the control zone in each membrane 130 will normally display a line after the source sample is added through the sample opening 140.

FIG. 8C illustrates the device 120 with a modified upper casing portion 146 having a plurality of apertures 148 each exposing a portion of the sample region 134 for receipt of the fluid sample with a dropper.

Figure 9:
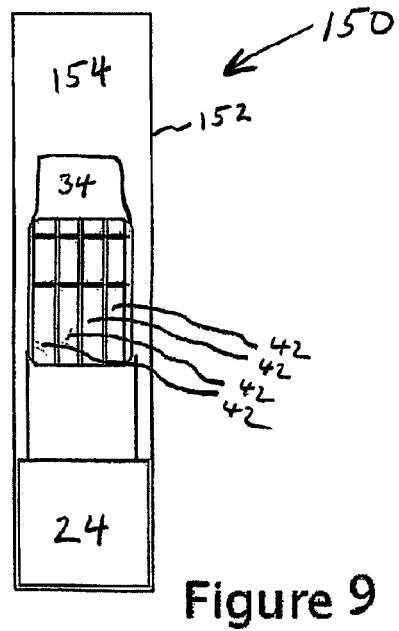
FIG. 9 provides a plan view of another design according to the invention.

FIG. 9 illustrates another device 150 formed on a substrate 152, having at one end an absorbent sample region 24 and at an opposing end a grip region 154 for being held while the sample region is dipped into a source sample. A plurality of test membranes 42 of the type illustrated in FIG. 2 are mounted in isolation from one another on the substrate 152 to individually receive fluid of the source sample. The membranes 42 each include a capture zone 44 and a control zone 48. An absorbing medium 34 may be situated near the thumb grip such that fluid of the sample migrates from each membrane 42 into the medium 34.

Figure 10:
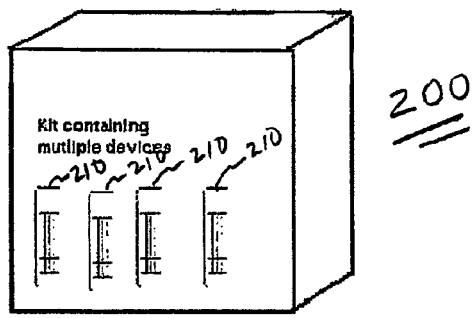
FIG. 10 illustrates a kit according to the invention.

Each of the aforedescribed rapid assay concentration devices, as well as other embodiments, is suitable for incorporation in a test kit such as the kit 200 shown in FIG. 10, for sequentially performing multiple assays. Depending on the target application, the kit 200 will comprise a variable number of such devices, generically referenced as devices 210, with appropriate package instructions for a person to sequentially assay samples from a source. In the case of monitoring hCG concentrations the kit 200 could be designed to provide the set of six possible outcomes illustrated in FIG. 11. A Level 1 positive response is indicated by formation of a band in one capture zone 44 and a band in each of the control zones 48. A Level 2 positive response is indicated by formation of a band in two capture zones 44 and a band in each of the control zones. A Level 3 positive response is indicated by formation of a band in each of three capture zones 44 and a band in each of the control zones 48. A Level 4 positive response is indicated by formation of a band in four of the capture zones 44 and a band in each of the control zones 48. A negative response is indicated when there is no band in any of the capture zones but bands are present in all of the control zones 48. An invalid response is indicated when one or more of the control zones does not develop a band.

Figure 11:
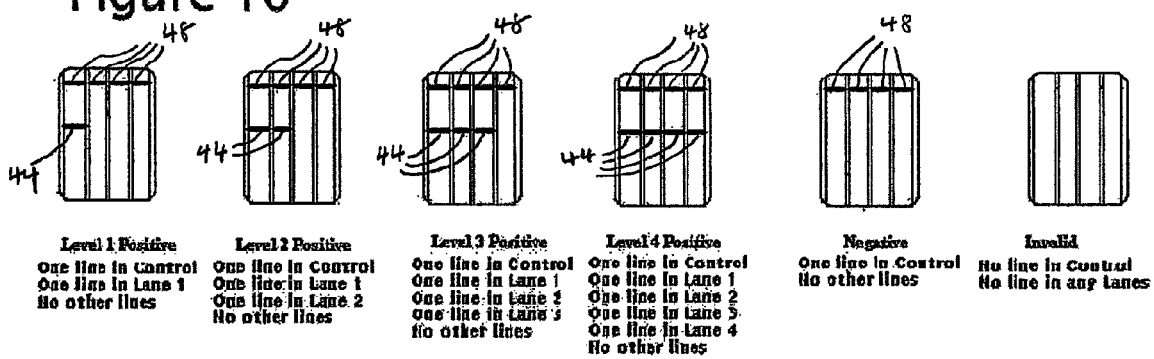
FIG. 11 illustrates a series of possible outcomes which may be provided by the invention.

FIGS. 12A through 12E illustrate combinations of possible sequenced hCG test results in accord with the responses shown in FIG. 11. The sequence of FIG. 12A includes testing with a device 210 every other day and results in a Level 4 positive response on day seven. The results indicate a doubling in hCG concentration every two days, which correlates with a healthy pregnancy. The sequence of FIG. 12B includes daily testing with the devices 210 after the second day, illustrating that the hCG levels are increasing but at a slower rate than evidenced in FIG. 12A.

The sequence of FIG. 12C also includes daily testing with the devices 210 after the second day, this time illustrating that the hCG levels are not exceeding a Level 1 positive response. The results may be indicative of an abnormality, warranting consultation with a physician. The sequence of FIG. 12D includes daily testing with the devices 210 after the second day, this time because there was a Level 3 positive response on the third day. Monitoring of such a rapid rise can be indicative of a multiple pregnancy. The sequence of FIG. 12E also includes daily testing with the devices 210 after the second day, illustrating that the hCG levels are initially increasing to a Level 2 positive response but then declining. This result may also be indicative of an abnormality, warranting consultation with a physician.

The foregoing illustrations demonstrate the value of providing a rapid assay concentration methodology for general use. Absent such a procedure it is much more difficult to identify potentially problematic trends in hCG levels.

When the methodology is provided for consumer use, e.g., monitoring an analyte level in urine, the devices should each be provided in a separate sealed container. However, the user should be instructed to (1) store all devices under similar sealed conditions to avoid environmental influences on test results (2) perform all tests under similar conditions; (3) provide source samples from first morning urine.

The particular methodology for using the device 210 for hCG testing will depend on whether it is provided in a midstream, cassette or dip stick format, in which case the procedure for using each type of device is similar to the procedure used in a corresponding similar format for a home pregnancy test kit. Due to the principles on which the levels are determined, the reading of the results may be valid for only a limited period of time, e.g., beginning at least three minutes after the test begins and ending ten minutes after the test begins.

Methods have been described for monitoring temporal changes of analyte levels in a source sample. Multiple test devices are provided, with each device capable of providing a response indicative of different threshold levels. Preferably the device includes multiple regions, each responsive at a different sensitivity level to indicate presence of the analyte in the source. Summarily, a first sample is brought into contact with a first test device to determine whether the source contains a level of analyte sufficient to induce a response thereto in one or more of the test unit regions. Subsequently, a second sample, possibly from the same source and collected under similar conditions, is brought into contact with a second of the test devices to determine the level of analyte in the second sample based on response thereto in one or more regions of the second test device. Third, fourth and additional samples can also be analyzed with additional devices in a similar manner as the first and second samples. Specifically, when samples are sequentially taken from the same source, the responses can indicate temporal changes in analyte concentration in the source. Thus by defining multiple measurably distinguishable sensitivity levels, each indicative of a different amount of analyte in the source, responses from the devices can provide information about variations in analyte concentrations and, if calibrated, will provide information about actual concentration levels.

Numerous examples of rapid assay concentration devices have been described. Multiple units of such devices may be provided in kit form to repeatedly perform assays of different samples from one or multiple sources in order to monitor and compare concentrations among sources or among samples from the same source. In one example method samples taken from a source at different times are analyzed with the rapid assay concentration devices to monitor changes in concentration of a target analyte. Another example use of the invention is for monitoring of PSA levels in blood. When physicians and other medical professionals do not have immediate access to laboratories, or have a need for quick results, the methods and devices disclosed herein may be used to assess analyte levels. More generally, methods and devices according to the invention may be adapted or directly applied to assess a wide variety of chemical conditions in, for example, the fields of health, environmental monitoring and medicine.

While specific applications and examples of the invention have been illustrated and discussed, the principles disclosed herein provide a basis for practicing the invention in a variety of ways and in a variety of applications. Because numerous possible variations are within the scope of the invention, the invention is only limited by the claims which now follow.

What is claimed is:

1. A method for monitoring whether an abnormal change occurs in a health condition based on whether a change in a level of analyte concentration occurs in a source, comprising:

providing multiple unitary test devices, each unitary test device including a plurality of regions, each region responsive at a different sensitivity level to indicate presence of the analyte in the source;

bringing a first sample from the source into contact with a first of the unitary test devices at a first time, there being a visually observable response in one or more regions of the first test device if the source contains at least a minimum level of analyte concentration; and subsequently bringing a second and different sample from the same source into contact with a second of the unitary test devices at a second time to determine whether a change in the health condition occurs based on whether an abnormal change in analyte level occurs by the second time, there again being a visually observable response in one or more regions of the second test device if the source contains at least a minimum level of analyte concentration, wherein determination of whether the health condition changes adversely is based on capillary flow of each sample from a sample receiving region on one of the first or second test devices to one or more of the plurality of regions on the same test device and the response on each device is based on an amount of binding of an antigen and an antibody to form complexes.

2. A method for monitoring abnormal changes in a health condition, comprising:

providing first and second lateral flow test units each of the type which includes a receiving zone for fluid samples separated from two or more regions, each region responsive to analyte migrating from the receiving zone by capillary flow into the region, the two or more regions on each test unit defining multiple measurably distinguishable sensitivity levels each distinguishable sensitivity level indicative of a different amount of analyte in a source;

the first test unit including a first region thereon responsive to the presence of analyte in the source at a first of the sensitivity levels and a second region responsive to presence of analyte in the source at a second of the sensitivity levels measurably distinguishable from the first of the sensitivity levels, wherein the first and second regions of the first test unit are responsive by binding an antigen and an antibody in order to identify presence of analyte in the source, the second test unit including a first region thereon responsive to the presence of analyte in the source at the first of the sensitivity levels and a second region responsive to presence of analyte in the source at the second of the sensitivity levels measurably distinguishable from the first of the sensitivity levels, wherein the first and second regions of the second test unit are responsive by binding an antigen and an antibody in order to identify presence of analyte in the source;

providing a first sample from the source at a first time;

bringing the first sample into contact with the receiving zone of the first unit to allow the first region thereon to receive a portion of the first sample by capillary flow from the receiving zone and provide an indication as to whether analyte is present in the first sample at least the first of the sensitivity levels;

providing a second sample from the source at a second time subsequent to providing the first sample to determine whether an adverse change in the health condition occurs; and bringing the second sample into contact with the receiving zone of the second unit to allow the first and second regions thereon to receive a portion of the second sample by capillary flow from the receiving zone and provide an indication as to whether analyte is present in the second sample at least one of the first and second sensitivity levels, wherein an abnormal difference between visually observable responses induced in the first test unit at the first time and induced in the second test unit at the second time, each based on binding of an antigen and an antibody, provides information about whether an adverse change in the health condition has occurred between the two times.

3. The method of claim 2 wherein the first unit includes a second region responsive to presence of the second level of analyte and the step of bringing the first sample into contact with the first unit includes allowing said second region to indicate whether analyte is present in the sample at least the second level.

4. The method of claim 2 wherein the step of providing the first test unit includes forming thereon at least three regions each responsive to the presence of analyte in the source at a different one of the multiple measurably distinguishable sensitivity levels.

5. The method of claim 4 wherein the step of providing the second test unit includes forming thereon at least three regions each responsive to the presence of analyte in the source at a different one of the multiple measurably distinguishable sensitivity levels.

6. The method of claim 5 wherein each of the regions of the first unit is responsive to substantially the same level of analyte as one of the regions of the second unit.

7. The method of claim 2 wherein the multiple measurably distinguishable sensitivity levels each indicative of a different amount of analyte in the source are defined by forming at least the first and second regions.

8. A method for determining whether an abnormal change is occurring in a health condition, comprising:

providing two or more test units each including multiple regions positioned thereon to receive analyte by capillary flow from a receiving zone, each region in each unit responsive to the presence of an analyte in a source at a sensitivity level measurably distinguishable from another region in the same test unit;

bringing a first sample from the source into contact with a first of the units to allow one or more of the regions thereon to indicate whether the analyte is present in the sample at least one of the levels; and on an occasion subsequent to providing the first sample, determining whether an adverse change occurs in the health condition by bringing a second sample from the source into contact with a second of the units to allow one or more of the regions thereon to indicate whether the analyte is present in the second sample at least one of the levels, wherein two or more of the regions on each unit are each responsive components in a ligand recognition system to provide different indications of analyte level allowing comparison of responses among regions on different test units based on levels of association of a detector reagent with a capture reagent resulting from migration of analyte from an associated receiving zone to the regions by capillary flow, wherein abnormal differences in indications on different test units provide evidence as to whether there has been an adverse change in the health condition.

9. The method of claim 8 wherein the step of providing one of the test units includes adhesively mounting the multiple regions on a substrate.

10. A method for determining an abnormal change in a health condition, comprising:

providing multiple unitary test devices, each unitary test device including a plurality of regions, each region being a responsive component in a ligand recognition system, based on capillary flow from a receiving zone, to a different sensitivity level to indicate presence of the analyte in a source without being determinative of a numerical concentration of the analyte in the source;

on a first occasion, bringing a sample from the source into contact with a first of the unitary test devices to induce a visually observable response thereto in one or more regions of the first test device when the source contains a predetermined minimum level of analyte concentration;

subsequently, on a second occasion, bringing a different sample from the same source into contact with a second of the unitary test devices to determine whether an adverse change has occurred in the health condition by inducing a visually observable response in one or more regions of the second unitary test device when the source contains a predetermined minimum level of analyte concentration; and comparing the visually observable response induced in the first test device directly with the visually observable response induced in the second test device to provide information about whether an abnormal change occurred in analyte level between the first and second occasions, this indicating occurrence of an adverse change in the health condition without requiring determination of analyte concentration in the source on either occasion.

11. The method of claim 10 wherein the first and second test devices are configured to indicate health of a pregnancy, and wherein the second occasion is at least one day after the first occasion, the method indicating abnormal health of the pregnancy based on whether analyte concentration has increased between the first and second occasions.

12. The method of claim 10 wherein the first and second test devices are configured to indicate presence of chorionic gonadotrophin as the analyte, and wherein the second occasion is at least 72 hours after the first occasion, the method indicating whether analyte concentration has doubled between the first and second occasions.

13. The method of claim 2 wherein the step of providing the first and second test units includes forming the first and second units separate and apart from one another.

14. The method of claim 8 wherein the step of providing two or more test units includes forming the test units separate and apart from one another.

* * * * *